United States Patent
Soum et al.

(10) Patent No.: US 9,862,666 B2
(45) Date of Patent: Jan. 9, 2018

(54) METHOD FOR OBTAINING POLYPHENOLS FROM A VEGETABLE RAW MATERIAL CONTAINING SAME

(71) Applicant: VALAGRO CARBONE RENOUVELABLE POITOU-CHARENTES, Poitiers (FR)

(72) Inventors: Stephane Soum, Migne-Auxances (FR); Antoine Piccirilli, Poitiers (FR); Frederic Bataille, Sevres-Anxaumont (FR)

(73) Assignee: VALAGRO CARBONE RENOUVELABLE POITOU-CHARENTES, Poitiers (FR)

( * ) Notice: Subject to any disclaimer, the term of this patent is extended or adjusted under 35 U.S.C. 154(b) by 0 days.

(21) Appl. No.: 14/443,535

(22) PCT Filed: Nov. 14, 2013

(86) PCT No.: PCT/FR2013/052739
§ 371 (c)(1),
(2) Date: May 18, 2015

(87) PCT Pub. No.: WO2014/076425
PCT Pub. Date: May 22, 2014

(65) Prior Publication Data
US 2015/0344390 A1    Dec. 3, 2015

(30) Foreign Application Priority Data
Nov. 16, 2012    (FR) ....................... 12 60916

(51) Int. Cl.
| | | |
|---|---|---|
| C07C 37/70 | (2006.01) | |
| C07C 37/68 | (2006.01) | |
| C07C 37/72 | (2006.01) | |
| C07D 307/80 | (2006.01) | |

(52) U.S. Cl.
CPC ............ *C07C 37/685* (2013.01); *C07C 37/72* (2013.01); *C07D 307/80* (2013.01)

(58) Field of Classification Search
CPC .................................................. C07C 37/70
See application file for complete search history.

(56) References Cited

U.S. PATENT DOCUMENTS

| | | |
|---|---|---|
| 6,824,797 B2 | 11/2004 | Goupy et al. |
| 7,368,144 B2 | 5/2008 | Lecoupeau et al. |
| 7,718,203 B2 | 5/2010 | Andre et al. |
| 8,372,445 B2 | 2/2013 | Giori et al. |
| 2002/0187207 A1 | 12/2002 | Goupy et al. |
| 2004/0096566 A1 | 5/2004 | Lecoupeau et al. |
| 2007/0243148 A1 | 10/2007 | Andre et al. |
| 2007/0258920 A1 | 11/2007 | Lecoupeau et al. |
| 2009/0191294 A1 | 7/2009 | Alkayali |
| 2009/0202667 A1 | 8/2009 | Giori et al. |
| 2013/0323372 A1 | 12/2013 | Msika et al. |

FOREIGN PATENT DOCUMENTS

| | | |
|---|---|---|
| EP | 1787970 | 5/2007 |
| EP | 1820492 | 8/2007 |
| FR | 2795965 | 1/2001 |
| FR | 2967586 | 5/2012 |
| JP | 2009203229 A * | 9/2009 |
| WO | 02-064536 | 8/2002 |
| WO | 2007-017037 | 2/2007 |

OTHER PUBLICATIONS

University of Texas at Austin. "Alcohol." © 2016. Available from: < http://colapret.cm.utexas.edu/courses/Nomenclature_files/alcohols.htm >.*
Ha et al., "Stilbenes and Oligostilbenes from Leaf and Stem of Vitis amurensis and Their Cytotoxic Activity," Archives of Pharmacal Research, vol. 32, No. 2, pp. 177-183, 2009.
Peralbo-Molina et al., "Comparison of extraction methods for exploitation of grape skin residues from ethanol distillation," Talanta, 101, pp. 292-298, Oct. 3, 2012.

* cited by examiner

*Primary Examiner* — Noble Jarrell
*Assistant Examiner* — John S Kenyon
(74) *Attorney, Agent, or Firm* — Young & Thompson

(57) ABSTRACT

A method for obtaining polyphenols from a vegetable raw material containing same, includes at least the following steps: optionally drying the raw material containing the polyphenols; crushing the raw material; defibrating the crushed raw material in an extruder in the presence of a solvent; separating the soluble phase from the fibers; and recovering the soluble phase, crude extract, containing the polyphenols.

22 Claims, No Drawings

METHOD FOR OBTAINING POLYPHENOLS FROM A VEGETABLE RAW MATERIAL CONTAINING SAME

This invention relates to obtaining polyphenols from a vegetable raw material containing same.

Polyphenols are natural molecules that are attracting increasing interest in numerous fields. Their antioxidant properties make possible in particular therapeutic applications particularly for the prevention and the treatment of cancers (as illustrated in, for example, YUN & al. "Pro- and Anti-Angiogenesis Effects of Resveratrol" In Vivo, 21 pages 365-370), and inflammatory, cardiovascular and neurodegenerative diseases. They are also used in the cosmetics industry as is described in, for example, the application EP1820492, or in agriculture as a stimulator of natural defenses, growth hormones, or biopesticides.

There are several natural vegetable sources of polyphenols, such as products of the vine, pine, tea, cocoa, apples, soybeans, flax, red fruits such as blueberries, cranberries, citrus fruits, hamamelis, gallnuts, sumac, heather, quebracho bark, chestnut bark, and oak bark, etc. The polyphenols, like the procyanidolic oligomers, stilbenes, lignans, catechins, chalcones, flavonoids, isoflavonoids, phenolic acids, resveratrol, viniferin, piceid, for example, make it possible for them to defend themselves against pathogenic agents.

Currently, the processes for extraction of polyphenols rest on the principle of maceration in a suitable solvent. These processes, described in particular in the applications FR2795965, EP1787970, or WO2007/017037, require contact at ambient temperature or under hot conditions; the use of a large amount of solvent and a purification stage in an alcohol solution is necessary after extraction. They are carried out intermittently, are long, costly, and demand a significant amount of energy for low extraction yields.

The application FR2967586 that describes a process for extraction of polyphenols from grape grounds is also known, with said process comprising a step of electrical treatment by pulsed power, and a diffusion of polyphenols in a solvent. It is also a matter of an intermittent process, implemented in units of very low capacity and representing heavy investment.

Finally, the application WO02064536 describes a process for extraction of polyphenols by Flash Détente and preparative chromatography. This Flash Détente process is by contrast suited for raw materials that are fragile and of low mechanical strength, and not for solid fibrous materials such as vine shoots, barks, seeds, and oilcake.

This invention has as its objective to remedy the drawbacks of the existing processes by proposing an effective process for obtaining polyphenols from a vegetable raw material containing same, necessitating the use of a small quantity of solvent, less costly and able to be carried out continuously.

For this purpose, the invention has as its object a process for obtaining polyphenols from a raw material containing same, comprising at least the following steps:
Optionally, drying the raw material,
Crushing the raw material,
Defibrating the raw material that is crushed in an extruder in the presence of a solvent,
Separating the soluble phase and fibers,
Recovering the soluble phase, crude extract, containing the polyphenols.

Advantageously, the process according to the invention makes it possible to obtain polyphenols in a significant amount with a small amount of solvent. For certain polyphenols, for example for the viniferin that is obtained from co-products of the vine, the amounts that are obtained are much larger than with previous processes.

The invention is now described in detail.

The object of the invention is a process for obtaining polyphenols from a raw material containing same.

This raw material can be selected in particular from pine barks, tea leaves, cocoa beans, and the products and/or co-products of the vine. Products and/or co-products of the vine are defined as grapes, in particular seeds and skins, vine shoots, vine leaves, vine stocks, stalks, grape grounds, and the fibers that are obtained from the production of grape juice. These different raw materials are designated as products and/or co-products in the vine in this description.

The process according to the invention comprises at least the following stages:
Optionally, drying the raw material containing polyphenols,
Crushing the raw material that is dried or that is naturally dry,
Defibrating the raw material that is crushed in an extruder in the presence of a solvent,
Separating the soluble phase and fibers,
Recovering the soluble phase, crude extract, containing the polyphenols.

Drying is necessary if the raw material is fresh, i.e., if it contains more than 30% moisture. If the raw material dried naturally and is mature, the drying step is not necessary.

It is important that the raw material be dried or dry to ensure a high flow rate during crushing and to prevent the jamming of the material in the extruder.

The drying can be done in an oven.

The moisture content in the raw material after drying or that is naturally dry is to be less than or equal to 30%.

The dried or dry raw material is then crushed.

The crushing can be done by any known means, for example using a crusher with blades or with hammers, or else by cryocrushing.

The crushing is to be done in such a way as to obtain a grain size of the raw material that is matched to the size of the extruder: if the particles are too large, there is a risk of jamming the extruder, and if the particles are too fine, the mechanical effect of the defibrating will not be optimal. For example, for a co-rotating twin-screw extruder whose length/diameter ratio is between 1 and 100 and more particularly between 20 and 40 and whose distance between centers is 21 mm, the grain size of the particles is to be between 1 and 10 mm, more particularly between 1 and 5 mm.

After crushing, the raw material is defibrated in an extruder in the presence of a solvent.

Preferably, the crushed raw material is mixed with an extraction solvent, and the mass is introduced into an extruder, for example using a gravimetric metering device.

The extruder is preferably a co-rotating twin-screw extruder.

An extruder consists primarily of one or more continuous screws rotating at a determined speed within a temperature-regulated cylindrical case.

The co-rotating twin-screw extruder consists of two co-penetrating screws rotating in the same direction and a case that encompasses these two screws. The latter are identical and consist of modules that comprise an element for conveying material that is equipped with windows or slots cut into the threads, with this element being called a counter thread. The twin-screw extruder makes it possible to produce in a single step a series of operations: defibrating, washing, chemical reaction, extrusion.

In the process according to the invention, the defibrating is therefore carried out by the conjunction of compression and shearing actions in the extruder.

This makes it possible to separate the fibers and the extraction solvent can extract polyphenols more easily and more quickly, and the amount of solvent that is to be used is consequently smaller than in the previous processes.

In a preferred way, the solvent that is used for the defibrating step is selected from among water, ethyl acetate, alcohols (methanol, ethanol, isopropanol, butanol, etc.), ketones (acetone, diethyl ketone, etc.), diols (propane-1,2-diol, propane-1,3-diol, etc.), glycols (dipropylene glycol, etc.). These solvents are used in pure form or in mixtures.

The solvent/dried or dry raw material ratio is preferably between 100 and 1,000%, preferably between 200 and 500%.

The extrusion step can be carried out at a temperature of between ambient temperature and 180° C. The mixing time prior to the introduction into the extruder can last from 1 minute to 4 hours, and the latency period from 0 to 2 hours.

As a function of the extraction solvent that is used, it is possible to adjust the pH by adding a basic solution or acid to said solvent to also improve the extraction.

After this stage of dynamic extraction by extrusion, it is necessary to separate the soluble part from the fibers.

The separation of the soluble part and the fibers can be done using a pressing case, mounted at the level of a compression zone in the extruder.

It is also possible to separate them at the extruder outlet by known techniques of filtration under nitrogen or pressing.

The soluble phase is then recovered. It involves crude extract that contains polyphenols.

After this step, the process according to the invention preferably comprises a step of concentration of polyphenols of the crude extract obtained in the soluble phase. This concentration of polyphenols can be carried out by evaporation of the solvent by heating or by freeze-drying.

The recovered crude extract contains a mixture of polyphenols. It can be used as such in a cocktail, or the different polyphenols can be separated and purified in particular by preparative chromatography on a column or by centrifugal partition chromatography (CPC).

The process according to the invention can therefore comprise an additional step of separation of the polyphenols from the extract. For example, when the raw material is a product or co-product of the vine, an attempt will be made to recover viniferin, trans-resveratrol and piceid.

According to an embodiment, after extraction of the polyphenols, the solid fraction that also contains cellulose that is not degraded can be used for the production of sugary juices by hydrolysis of the cellulose into glucose and then the production of ethanol by fermentation.

Advantageously, the process according to the invention is simple, continuous, economical, and does not require the use of much solvent in comparison to previous processes. In addition, it makes it possible to recover large amounts of polyphenols. For viniferin in particular, the yields that are obtained are to a large extent greater than those obtained until then.

The invention is now illustrated by tests carried out with the process according to the invention and comparison tests with previous methods.

1. Example of the Process According to the Invention for the Extraction of Viniferin and Trans-Resveratrol From Melon De Bourgogne Vine Shoots Dried Melon de Bourgogne vine shoots are crushed to 1, 4 or 8 mm by a crusher with blades.

The crushed shoots are mixed for 15 minutes with an extraction solvent that consists of 80% ethanol and 20% water.

The mixture is then introduced using a gravimetric metering device in a co-rotating twin-screw extruder Clextral BC21 at 60° C. The speed of rotation of the screws is 100 rpm, and the flow rate of the metering device is 2 kg/h.

The separation of the solvent and fibers is carried out using a pressing case that is mounted at the level of a compression zone.

Next, the amounts of viniferin and trans-resveratrol that are present in the recovered crude extract are determined by HPLC chromatography.

The results that are obtained are presented in Table 1.

TABLE 1

| | 16 Weeks | | | 24 Hours |
|---|---|---|---|---|
| Latency Period According to the Size of the Vines | | | | |
| Grain Size, mm | 1 | 4 | 8 | 8 |
| Extraction Solvent (V/V) | Ethanol/Water (80/20) | | | |
| Extraction Temperature, ° C. | 60 | | | |
| Extraction Atmosphere | Nitrogen | | | |
| Evaporation | Rotary Evaporator Under Nitrogen | | | |
| Content of Trans-Resveratrol, ppm | 764 | 915 | 387 | 207 |
| Content of Viniferin, ppm | 5,482 | 8,170 | 6,440 | 2,035 |

2. Comparison Results for the Extraction of Viniferin and Trans-Resveratrol With the Process According to the Invention and a Process of the Prior Art From Melon De Bourgogne Vine Shoots Two comparison tests are carried out:

A process of the prior art: dynamic extrusion by infusion,

The process according to the invention.

Dynamic Extrusion by Infusion:

The shoots are crushed to 1 mm and are introduced into a three-neck reactor equipped with a stirring system and a nitrogen bubbling system. Reflux extraction is carried out for 2 hours with a solvent that consists of 80% ethanol and 20% water, at 60° C.

The separation of the solvent and fibers is done on a filter press.

Process According to the Invention:

Dried Melon de Bourgogne vine shoots are crushed to 4 mm by a crusher with blades.

Crushed shoots are mixed for 15 minutes with an extraction solvent that consists of 80% ethanol and 20% water.

The mixture is then introduced using a gravimetric metering device into a co-rotating twin-screw extruder Clextral BC21 at ambient temperature. The speed of rotation of the screws is 100 rpm, and the flow rate of the metering device is 2 kg/h.

The separation of the solvent and fibers is done using a pressing case mounted at the level of a compression zone.

In the two cases, the amounts of viniferin and trans-resveratrol that are present in the crude extract that is recovered are then determined by HPLC chromatography.

The results that are obtained are presented in Table 2.

TABLE 2

| | Process | |
|---|---|---|
| | Process According to the Invention | Dynamic Extraction by Infusion |
| Grain Size, mm | 4 | 1 |
| Target Extrusion Temperature, ° C. | T ambient | 60 |
| Extraction Solvent (V/V) | Ethanol/Water (80/20) | Ethanol/Water (80/20) |
| Trans-Resveratrol Content, ppm | 984 | 764 |
| Viniferin Content, ppm | 7,400 | 5,482 |

The invention claimed is:

1. A process for obtaining polyphenols from raw plant material containing same, the process comprising at least the following steps:
    optionally, drying the raw material containing polyphenols,
    crushing the raw material that is dried or that is naturally dry,
    defibrating the crushed raw material in an extruder in the presence of a solvent,
    separating the soluble phase and fibers, and
        recovering the soluble phase crude extract, containing the polyphenols,
    wherein separating the soluble phase and fibers is carried out in the extruder using a pressing case mounted at the level of the compression zone.

2. The process for obtaining polyphenols according to claim 1, further comprising concentrating the polyphenols of the crude extract obtained in the soluble phase.

3. The process for obtaining polyphenols according to claim 2, wherein concentrating the polyphenols of the crude extract is carried out by evaporation of the solvent by heating or by freeze-drying.

4. The process for obtaining polyphenols according to claim 1, wherein the solvent/raw material ratio in the extruder is between 100 and 1,000% by weight.

5. The process for obtaining polyphenols according to claim 1, wherein the solvent is selected from the group consisting of water, ethyl acetate, alcohols, ketones, diols, glycols and mixtures thereof.

6. The process for obtaining polyphenols according to claim 1, wherein the solvent and the crushed raw material are mixed before being introduced into the extruder for 1 minute to 4 hours.

7. The process for obtaining polyphenols according to claim 1, wherein the temperature in the extruder is between ambient temperature and 180° C.

8. The process for obtaining polyphenols according to claim 1, wherein the raw material is dried in the drying step to a moisture content of less than or equal to 30%.

9. The process for obtaining polyphenols according to claim 1, wherein the raw material is selected from the group consisting of pine bark, tea leaves, cocoa beans, products of grape vine, and mixtures thereof.

10. The process for obtaining polyphenols according to claim 1, wherein the raw material is a product of the grape vine, and wherein the polyphenols are stilbenes.

11. The process for obtaining polyphenols according to claim 10, wherein the polyphenols are at least one of viniferin, trans-resveratrol, and piceid.

12. A process for obtaining polyphenols from a raw plant material containing same, the process comprising at least the following steps:
    optionally, drying the raw material containing polyphenols,
    crushing the raw material that is dried or that is naturally dry,
    defibrating the crushed raw material that is crushed in an extruder in the presence of a solvent,
    separating the soluble phase and fibers, and
        recovering the soluble phase crude extract, containing the polyphenols,
    wherein the step of separating the soluble phase and fibers is carried out after extrusion by filtration.

13. The process for obtaining polyphenols according to claim 12, further comprising concentrating the polyphenols of the crude extract obtained in the soluble phase.

14. The process for obtaining polyphenols according to claim 12, wherein the solvent is selected from the group consisting of water, ethyl acetate, alcohols, ketones, diols, glycols and mixtures thereof.

15. The process for obtaining polyphenols according to claim 12, wherein the temperature in the extruder is between ambient temperature and 180° C.

16. A process for obtaining polyphenols from raw plant material containing same, the process comprising at least the following steps:
    optionally, drying the raw material containing polyphenols,
    crushing the raw material that is dried or that is naturally dry,
    defibrating the crushed raw material that is crushed in an extruder in the presence of a solvent,
    separating the soluble phase and fibers, and
        recovering the soluble phase crude extract, containing the polyphenols,
    wherein the raw material is a product of grape vine, and wherein the polyphenols are stilbenes.

17. The process for obtaining polyphenols according to claim 16, further comprising concentrating the polyphenols of the crude extract obtained in the soluble phase.

18. The process for obtaining polyphenols according to claim 16, wherein the solvent is selected from the group consisting of water, ethyl acetate, alcohols, ketones, diols, glycols and mixtures thereof.

19. The process for obtaining polyphenols according to claim 16, wherein the temperature in the extruder is between ambient temperature and 180° C.

20. The process for obtaining polyphenols according to claim 16, wherein the polyphenols are at least one of viniferin, trans-resveratrol, and piceid.

21. The process for obtaining polyphenols according to claim 12, wherein the step of separating the soluble phase and fibers is carried out after extrusion by filtration under nitrogen or by pressing.

22. The process for obtaining polyphenols according to claim 10, wherein the raw material is selected from the group consisting of grape seeds, grape skins, grape vine shoots, grape vine leaves, grape vine stocks, grape vine stalks, grape grounds, and fibers that are obtained from production of grape juice.

* * * * *